United States Patent [19]
Kimura et al.

[11] 4,360,933
[45] Nov. 30, 1982

[54] URINE SUCTION AND COLLECTION DEVICE FOR A VACUUM SUCTION TYPE URINATING AID

[75] Inventors: Ryusuke Kimura, Ichikawa; Shuichi Saito, Funabashi; Kenshun Ishii, Tokyo, all of Japan

[73] Assignee: Kimura Bed Mfg. Company Limited, Tokyo, Japan

[21] Appl. No.: 179,878

[22] Filed: Aug. 20, 1980

[30] Foreign Application Priority Data

Jun. 8, 1980 [JP] Japan .............................. 55-79773[U]
Jun. 8, 1980 [JP] Japan .............................. 55-79774[U]
Jun. 13, 1980 [JP] Japan .............................. 55-82621[U]

[51] Int. Cl.³ .............................................. E03D 13/00
[52] U.S. Cl. ........................................... 4/301; 4/316; 4/144.1; 4/144.3; 4/144.4
[58] Field of Search ................ 4/144.3, 301, 300, 316, 4/144.1, 144.2, 144.3, 144.4

[56] References Cited

U.S. PATENT DOCUMENTS

| | | | |
|---|---|---|---|
| 2,749,558 | 6/1956 | Lent et al. | 4/144.3 |
| 2,968,046 | 1/1961 | Duke | 4/144.3 |
| 3,034,131 | 5/1962 | Lent | 4/316 X |
| 3,329,974 | 7/1967 | Balasco et al. | 4/301 |
| 3,340,543 | 9/1967 | Cella | 4/316 |
| 3,533,109 | 10/1970 | Kishimoto | 4/301 |
| 3,995,328 | 12/1976 | Carolan et al. | 4/316 |
| 4,050,103 | 9/1977 | Nakao et al. | 4/144.3 |
| 4,063,315 | 12/1977 | Carolan et al. | 4/316 |
| 4,202,057 | 5/1980 | Ibarra | 4/144.3 |
| 4,202,058 | 5/1980 | Anderson | 4/144.3 |
| 4,275,470 | 6/1981 | Bodger et al. | 4/316 |

*Primary Examiner*—Henry K. Artis
*Attorney, Agent, or Firm*—Wenderoth, Lind & Ponack

[57] ABSTRACT

A urine suction and collection device for a vacuum suction type urinating aid which contains a urine receiver provided with a urine suction opening to be applied to a urinating region includes, a urine transport tube connected, at one end, with the urine receiver and connected, at the other end, with a urine tank, and a vacuum suction tube communicating with a vacuum suction device and, connected to the top of the urine tank. The vacuum comprising: said vacuum suction device positioned in a housing at the one side thereof. A cover fastened to the top of the housing at the other side thereof freely pivots around an axis at one end of the cover. Urine feed ports and air suction ports respectively are provided at the top of the urine tank put in the housing and at the bottom of the cover, and the urine feed port and the air suction port of the cover respectively are connected to the urine transport tube and the vacuum suction tube through passages in the cover.

18 Claims, 15 Drawing Figures

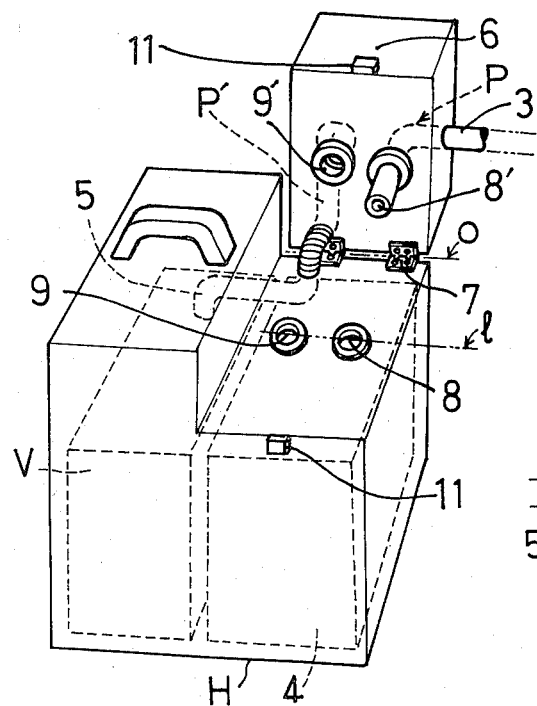
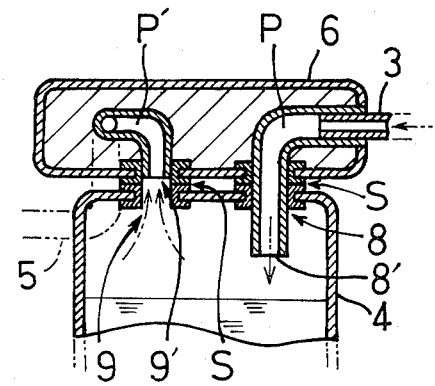
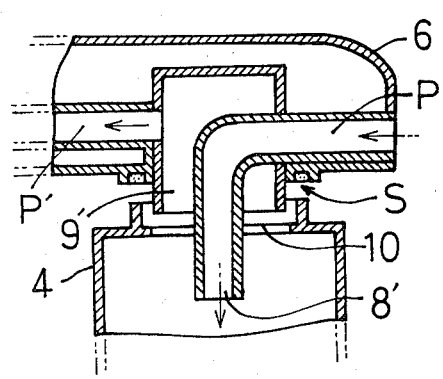
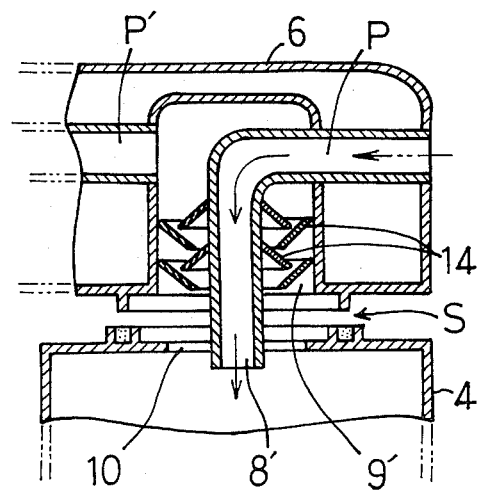
FIG. 2
FIG. 3
FIG. 4(a)
FIG. 4(b)

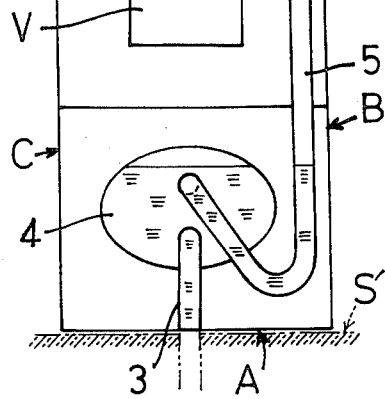
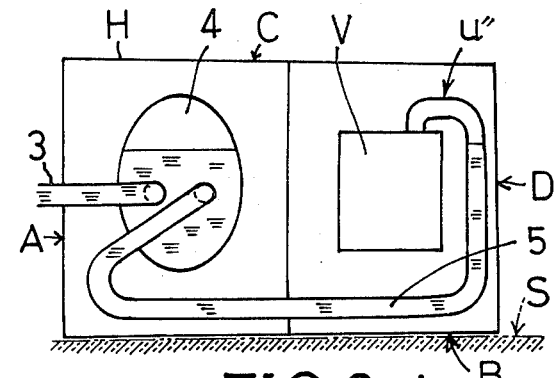
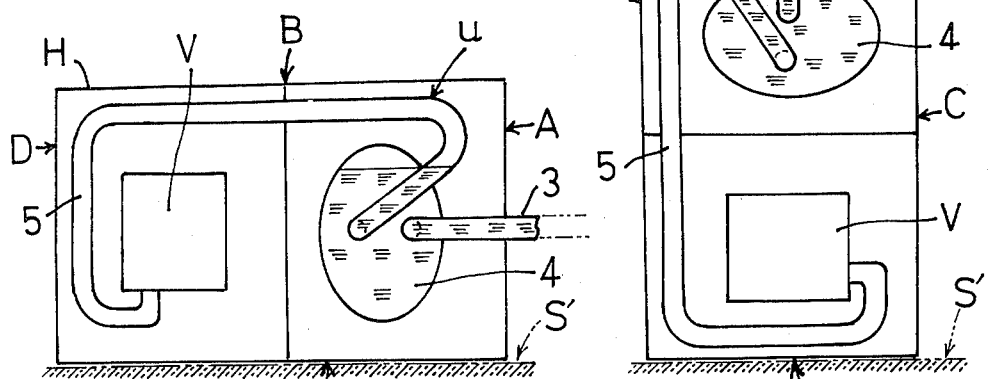
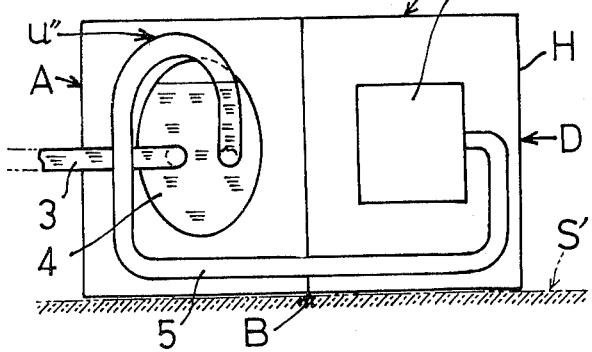

URINE SUCTION AND COLLECTION DEVICE FOR A VACUUM SUCTION TYPE URINATING AID

BACKGROUND OF THE INVENTION

The present invention relates to a urine suction and collection device for a vacuum suction type urinating aid.

There are people who must be assisted in urinating in bed. These people include the old lying in bed, serious patients, patients suffering from an incontinence of urine who cannot control their urination as soon as they feel a desire to urinate, and patients who cannot go to the toilet alone.

To attain the objective of assistance, there has been employed an apparatus in which a receiver applied to the urinating region of the patient to receive his urine is connected with a tank to collect the urine through a tube. However, with the conventional apparatus, the urine received by the receiver is dropped into the tank through the tube simply by gravity, and therefore the tube and the tank must be placed below the receiver, to permit urine to be dropped. For example, if the patient changes his position, causing the tube to placed even partially above the receiver, the urine in the tube flows back into the receiver, to soak the patient and bedclothes inconveniently. Such a conventional apparatus is disadvantageously restricted with respect to the place of use and urinating pose.

SUMMARY OF THE INVENTION

The urinating aid of the present invention receives the urine of the patient in a urine receiver applied to his urinating region, and transports it to a urine tank through a urine transport tube forcedly together with air by vacuum suction, thereby overcoming perfectly the disadvantage of the conventional apparatus. In other words, even when the urine transport tube and the urine tank cannot be placed below the urine receiver, the present invention allows urine to be transported into the urine tank, without causing it to back at all.

The present invention combines a vacuum suction device and a urine tank of such a vacuum suction type urinating aid very reasonably and positions them together in a housing, to simplify the appearance and provide a compact construction as a whole. Moreover, in the present invention, the urine transport tube communicating to the urine receiver and the vacuum suction tube communicating to the vacuum suction device can be connected or disconnected with the urine tank by simple operation through the cover of the housing, and therefore it is very easy to unload a urine tank full of urine from the housing and to load an empty urine tank into the predetermined position of the housing. In addition, in the present invention, even if the housing is caused to turn over or to fall erroneously with the urine tank full of urine, the urine in the urine tank is prevented from reaching the vacuum suction device through the vaccum suction tube, by a very simple and reasonable structure, thereby preventing trouble to the vacuum suction device caused by water.

BRIEF DESCRIPTION OF THE DRAWINGS

The present invention is described below with detail in reference to the accompanying drawings which show embodiments the invention.

FIG. 1 (b) is an illustrative perspective view to show the state of use of the urinating aid.

FIG. 2 is an illustrative perspective view to show an embodiment of the urine suction and collection device of the present invention.

FIG. 3 is an illustrative sectional view of a main portion of the embodiment shown in FIG. 2.

FIGS. 4 (a) and (b) are illustrative sectional views of other embodiments of the main portion.

FIGS. 9 (a), (b), (c) and (d) are schematic side views illustrating the device shown in FIG. 6 (a) oriented in various positions.

FIG. 10 is a schematic side view to show the condition of the device shown in FIG. 8 oriented in a different position.

DETAILED DESCRIPTION OF THE INVENTION

Figure 1A:
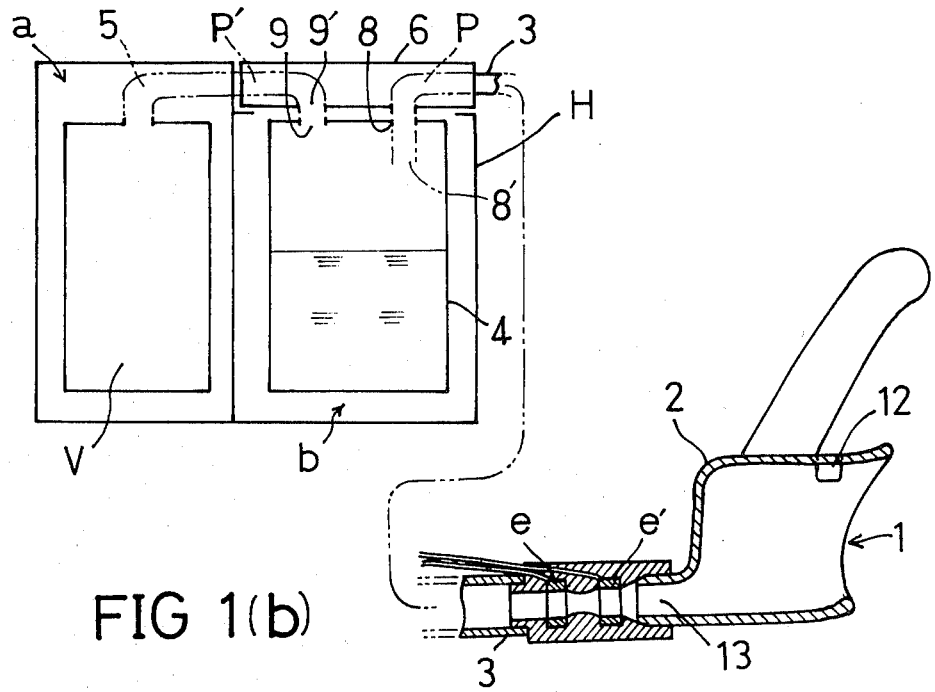
FIG. 1 (a) is a sectional view of a schematic illustration to shown an embodiment of the general composition of the vacuum suction type urinating aid according to the present invention.
Figure 1B:
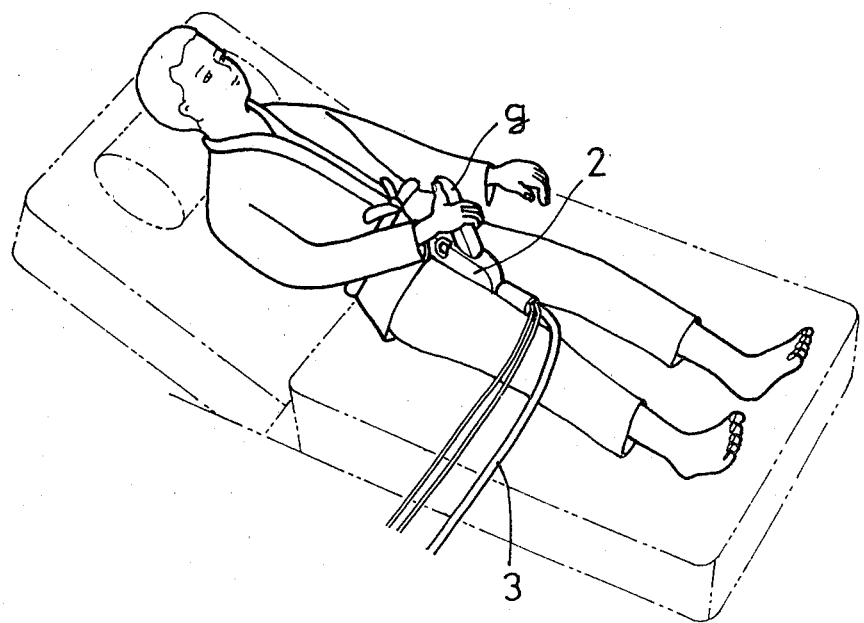

FIG. 1 shows an embodiment of the general composition of the vacuum suction type urinating aid of the present invention. Such vacuum suction type urinating aid comprises a urine receiver 2 provided with a urine suction opening 1 at the front side, a urine transport tube 3 connected, at one end, with the rear side of the urine receiver 2 and connected, at the other end, with a urine tank 4, and a vacuum suction tube 5 communicating with a vacuum suction device V and connected to the top of urine tank 4. The present invention puts the urine tank 4 and the vacuum suction device V together into a housing H very easily. The composition is as described below. Symbol H indicates a housing in which vacuum suction device V is positioned in one side or compartment a, and a cover 6 is fastened to the top of housing H to cover another side or compartment b, for example by hinges 7, at one end of the cover 6, to be able to pivot. Symbol 4 indicates a urine tank which is put in the housing H in the other side or compartment b by opening cover 6. In the top of urine tank 4 and the bottom of cover 6, corresponding urine feed ports 8 and 8' and corresponding air suction ports 9 and 9' are formed. The urine feed port 8' and the air suction port 9' of the cover 6 are respectively connected through passages P and P' in the cover 6 to urine transport tube 3 and vacuum suction tube 5. The urine feed port 8' and the air suction port 9' of cover 6 and the corresponding urine feed port 8 and the corresponding air suction port 9 at the top of the urine tank 4 can be formed at proper positions. For example, in the embodiment shown in FIGS. 2 and 3, urine feed ports 8 and 8' and said air suction ports 9 and 9' are formed on the line 1 parallel to the pivotal axis O of the cover 6, so that when cover 6 is closed, the urine feed ports 8 and 8' and the air suction ports 9 and 9' may be connected and sealed simultaneously. In the embodiment shown in FIGS. 4(a) and 4(b) the urine feed port and the air suction port to be formed in the urine tank 4 are formed as a common opening 10, and at the bottom of cover 6 corresponding to opening 10, the external air suction port 9' and the urine feed port 8' protruded coaxially in air suction port 9' are provided. The embodiment shown in FIGS. 2 and 3 have two sealing members S, while the embodiment shown in FIGS. 4 has only one sealing member S, to allow advanced sealing easily as a feature of the latter embodiment. The connection between the urine feed port 8' and the urine transport tube 3 and the connection between the air suction port 9' and the vacuum suction tube 5 can be made in a suitable manner. The sealing structure also can be selected suitably.

In this composition of the present invention, after an empty urine tank 4 is put in the predetermined position at the other side b of the housing H, the cover 6 is closed, and the urine feed ports 8 and 8' and the air suction ports 9 and 9' are connected and sealed, cover 6 being locked by a proper lock 11.

When a patient feels a desire to urinate, he takes a handle g provided at a proper place on the urine receiver 2, to apply the urine suction opening 1 to the urinating region, and urinates into the urine receiver 2 in this state. Immediately before or after this action, a manual switch (not illustrated) provided at handle g, or a drop in the resistance value between a pair of electrodes e and e' in a urine passage near the urine receiver 2 due to the presence thereof of urine is detected, to turn on an automatic switch, for starting the vacuum suction device. Then vacuum pressure is applied to the urine receiver 2 through the vacuum suction tube 5, the passage P', the air suction ports 9' and 9, the urine tank 4, the urine feed ports 8 and 8', the passage P and the urine transport tube 3. Therefore, the urine discharged through urine suction opening 1 into the urine receiver is sucked by the vacuum suction forcedly from the urine outlet 13 into the urine transport tube 3, together with and by air sucked into the urine receiver 2 from a clearance between the urine suction opening and the urinating region and an air suction hole properly formed in the urine receiver 2, and is discharged into the urine tank 4 through the urine transport tube 3, the passage P and the urine feed ports 8 and 8'. The air is fed from the top of the urine tank 4 through the air suction ports 9 and 9', the passage P', and the vacuum tube 5 into the vacuum suction device V, to be discharged, while urine is separated from air by gravity, to be collected in the urine tank 4.

In the embodiment shown in FIGS. 4(a) and 4(b) the air suction port 9' and the urine feed port 8' of the cover 6 are provided coaxially. In this case, if the protrusion of the urine feed port 8' is long, there is no problem. But if it is short, thorough separation of water from air cannot be made, allowing water to be sucked from the urine feed port 8' by the air suction port 9'. To prevent such inconvenience with a short protrusion of the urine feed port 8', baffle boards 14 can be fitted between the air suction port 9' and the urine feed port 8' as shown in the embodiment of FIG. 4 (b). Baffle boards 14 can be protruded downward alternately from the respective walls of the air suction port 9' and the urine feed port 8' toward the opposite walls, or they can be formed by any other structure such as meshes, as long as they divert air current to separate water particles from air. The present invention can prevent the trouble to the vacuum suction device V caused by water, by minimizing the water sucked into the air suction port 9' by the vacuum pressure during ordinary use, in this manner.

In the present invention, the urine of a patient is thus sucked, transported and discharged into the urine tank 4, but when a predetermined amount of urine is collected in the urine tank 4 after several times of use, lock 11 is released, to open the cover 6, and the urine tank 4 can be unloaded from the housing H. Thus, the urine collected in the urine tank 4 can be cast away, to empty the tank, and the urine tank 4 can be loaded in the housing H again for re-use. In this case, in the present invention, urine transport tube 3 and vacuum suction tube 5 are not connected directly with the urine tank 4, but are connected indirectly through the urine feed port 8' and the air suction port 9' formed at the bottom of the cover 6, and they can be sealed and connected just by closing the cover 6. Therefore, the urine tank 4 can be unloaded and loaded after being emptied just by opening and closing the cover 6 very simply and easily, as a feature of the present invention.

Figure 5:
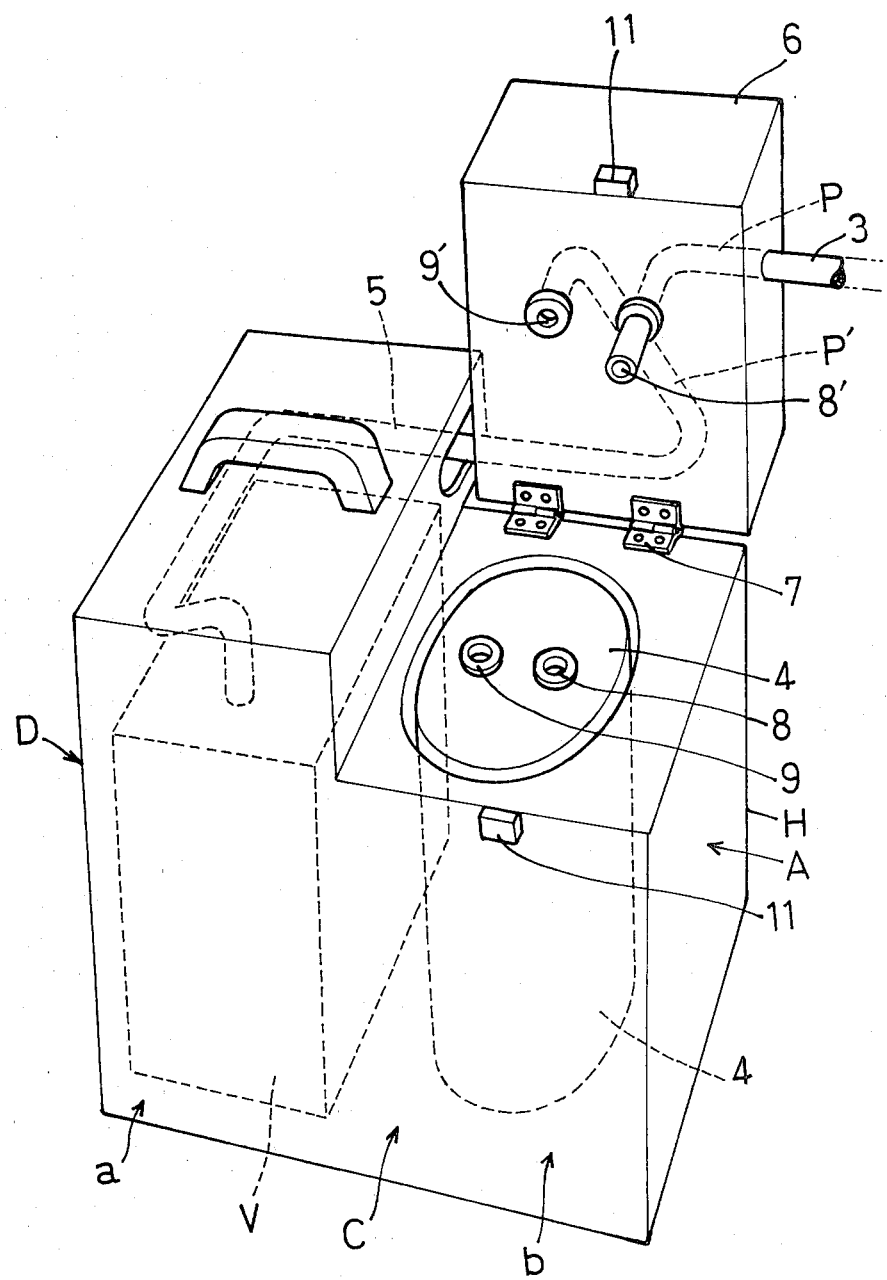
FIG. 5 is an illustrative perspective view to show another embodiment of the urine suction and collection device of the present invention.
Figure 6A:
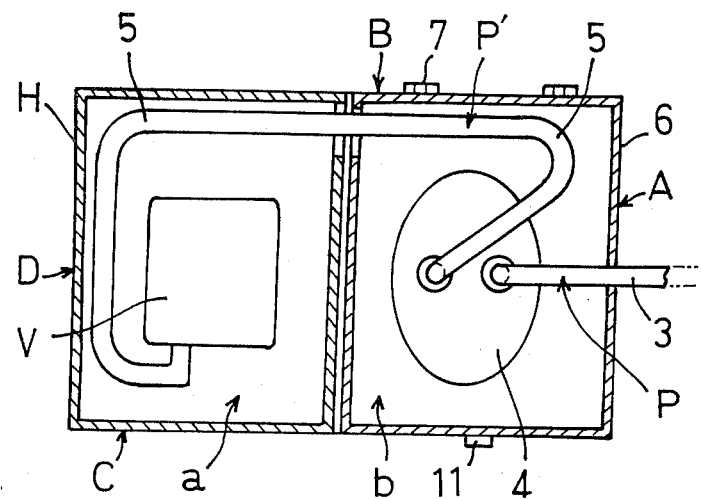
FIGS. 6 (a) and (b) are respectively an illustrative transverse sectional view and an illustrative longitudinal sectional view of the embodiment shown in FIG. 5.
Figure 6B:
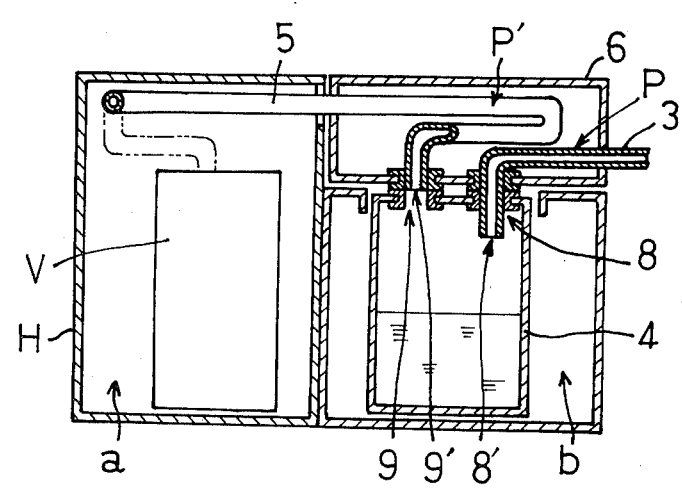
Figure 7:
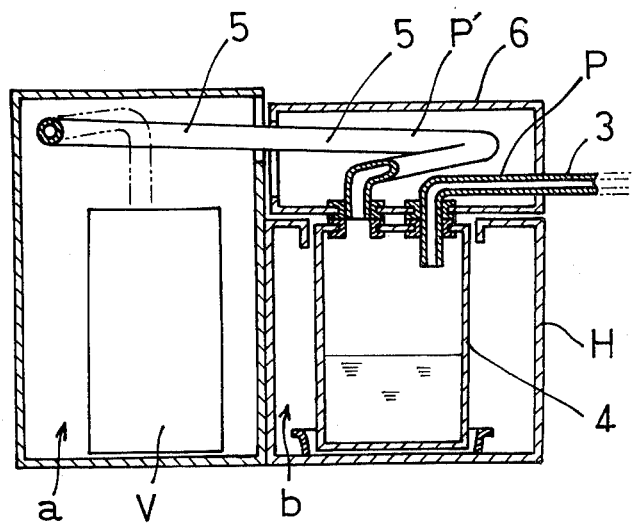
FIG. 7 is an illustrative longitudinal sectional view of a further embodiment of the main portion.
Figure 8:
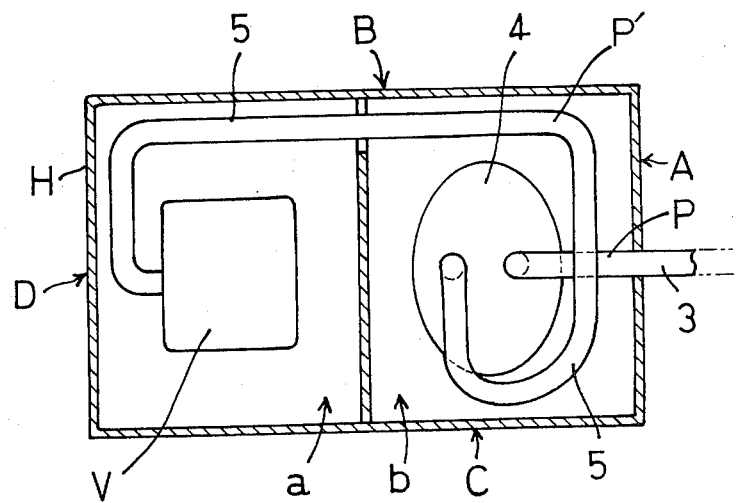
FIG. 8 is an illustrative transverse sectional view of a further embodiment of the main portion.

As described above, since the vacuum suction device V and the urine tank 4 are positioned together in the housing H in the present invention, turning over or falling of the housing H with urine collected in the urine tank 4 may cause the joint between the vacuum suction device V and the vacuum suction tube 5 to be lower than the liquid level of the urine tank 4. The embodiments of the present invention shown in FIG. 5 and the other additional drawings perfectly prevent the urine collected in the urine tank 4 from entering into the vacuum suction device V through the vacuum suction tube 5 in whatever direction position or orientation housing H may have. In these embodiments, vacuum suction tube 5 is arranged transversely outside the urine tank 4. In the embodiment shown in FIGS. 5 and 6 (a), said vacuum suction tube 5 is arranged outside urine tank 4 toward the right side face (side face A in the illustration and to the top side face (side face B) at the other side b of the housing H, and is arranged outside urine tank 4 toward the bottom side face (side face C in the illustration) at the one side a. In the embodiment shown in FIG. 8, at the other side b of the housing H, tube 5 is arranged outside urine tank 4 toward side face A, face B and also side face C. In these embodiments, the direction of the vacuum suction tube 5 toward the left side face (side face D) of the housing H in the illustrations is of course transversely outside the urine tank 4. The vacuum suction tube 5 connecting the vacuum suction device V with the top of the urine tank 4 can take any route and composition, as long as it is arranged transversely outside the urine tank 4. In these embodiments, the connection between the urine tank 4 and the vacuum suction tube 5 and the connection between the urine tank 4 and the urine transport tube 3 are not always required to be made indirectly through the cover 6, but can be made directly.

Thus, in these embodiments, even if the housing H falls or tips or is turned over, the urine in the urine tank 4 can be prevented from entering into the vacuum suction device V, by the following action. If the housing H falls with its side face A in contact with the floor S' as shown in FIG. 9 (a), the urine in the urine tank 4 flows into the vacuum suction tube 5, but does not rise beyond the urine tank 4, and therefore, it does not reach the one side a and does not reach the vacuum suction device V. If the housing H falls with side face C or D in contact with the floor S respectively as shown in FIGS. 9 (c) and (d), the uppermost portion u or u' of the vacuum suction tube 5 in the respective cases is positioned above the uppermost portion of the urine tank 4, and urine cannot reach the uppermost portion u or u', and remains at the other side a of the housing H and is prevented from entering the vacuum suction device V. When the housing H falls with its side face B in contact with the floor S as shown in FIG. 9 (b), urine flows into the vacuum suction tube 5 at the one side a of the housing H, but since the uppermost portion u" of the vacuum suction tube 5 is above the uppermost portion of the urine tank in the route to the vacuum suction device V, urine does not reach the vacuum suction device V. In this case, as shown in FIG. 10, if uppermost portion u" is formed at the other side b of the housing H, the quantity of urine flowing into the vacuum suction tube 5 can be less than in the case of FIG. 9 (b). Then, to raise up the fallen housing H, if the vacuum suction tube 5 on the urine tank 4 side is kept lower than that on the vacuum suction device V side, urine can be prevented perfectly from reaching the vacuum suction device V when the housing H is raised up. In this case, if the vacuum suction tube 5 is formed to incline upwardly from the urine tank 4 side to the vacuum suction device V side, all the urine in the vacuum suction tube 5 can be returned to the urine tank 4, just by raising up the housing H. Thus, in these embodiments, even if the housing H falls in any direction by any error when the vacuum suction device is not operated, urine in the urine tank 4 can be perfectly prevented from entering through the vacuum suction tube 5 into the vacuum suction device V, to perfectly prevent trouble to the vacuum suction device V caused by water.

As described above in detail, the vacuum suction type urinating aid of the present invention has a feature that even when the urine transport tube and the urine tank cannot be placed below the urine receiver, urine can be collected perfectly in the urine tank without causing the urine to flow back, and therefore that a patient can urinate while lying in bed with no restriction on the place of use or urinating pose, since the urine received by the urine receiver applied to the urinating region of the patient is transported forcedly together with air in the urine transport tube by vacuum suction to the urine tank. The urine suction and collection device of the present invention for the vacuum suction type urinating aid has a feature that the vacuum suction device and the urine tank are combined very reasonably and put together into a housing, to simplify the apperance in a compact composition as a whole. One embodiment has the feature that since the urine transport tube communicating to the urine receiver and the vacuum suction tube communicating to the vacuum suction device are respectively connected to the urine tank through a cover of the housing, the unloading of a urine tank full of urine and the loading of an empty urine tank can be made by a very simple operation. In another embodiment, during the operation of the vacuum suction device, water sucked into the urine tank through the urine transport tube is prevented from being sucked together with air through the vacuum suction tube into the vacuum suction device. In a further embodiment, even if the housing falls in any direction when the vacuum suction device is not operated, urine in the urine tank can be perfectly prevented from entering into the vacuum suction device, by arranging the vacuum suction tube connecting the urine tank with the vacuum suction device in a particular manner, thereby preventing trouble to the vacuum suction device due to water.

What is claimed is:

1. A urine suction and collection device for use with a vacuum suction type urinating aid of the type including a urine receiver with a urine suction opening to be applied to a urinating region of a patient, said urine suction and collection device comprising:

a housing having first and second laterally spaced areas;

a suction device for generating a vacuum, said suction device being positioned in said first area of said housing;

a urine tank positioned in said second area of said housing;

a cover pivotally connected to said housing for selective pivotal movement between a first position covering said second area and a second position uncovering said second area whereat said urine tank may be inserted into and removed from said second area;

a urine transport tube having a first end adapted to be connected to a urine receiver of a vacuum suction type urinating aid and a second end;

a vacuum suction tube having a first end connected to said suction device and a second end;

means in the bottom of said cover for supporting said second ends of said urine transport tube and said vacuum suction tube; and opening means in the top of said urine tank for communication therethrough of said second ends of said urine transport tube and said vacuum suction tube when said cover is in said first position thereof;

whereby pivotal movement of said cover between said first and second positions thereof moves said second ends of said urine transport tube and said vacuum suction tube away from said opening means.

2. A device as claimed in claim 1, wherein said first and second areas comprise first and second laterally separated compartments in said housing.

3. A device as claimed in claim 1, wherein said opening means comprise first and second openings in said top of said urine tank, and said supporting means comprise first and second passages extending through said cover and having first ends respectively connected to said second ends of said urine transport tube and said vacuum suction tube and second ends respectively opening downwardly into said first and second openings when said cover is in said first position thereof.

4. A device as claimed in claim 3, wherein said second end of said first passage extends through said first opening in said top of said urine tank and protrudes into said urine tank when said cover is in said first position thereof.

5. A device as claimed in claim 3, further comprising first and second seals respectively sealing said second end of said first passage and said first opening and said second end of said second passage and said second opening when said cover is in said first position thereof.

6. A device as claimed in claim 1, wherein said opening means comprises a single opening in said top of said urine tank, and said supporting means comprise first and second passages extending through said cover and having first ends respectively connected to said second ends of said urine transport tube and said vacuum suction tube and second ends opening downwardly into said single opening when said cover is in said first position thereof, said second end of said first passage being positioned coaxially within said second end of said second passage.

7. A device as claimed in claim 6, wherein said second end of said first passage extends through said single opening and protrudes into the interior of said urine tank when said cover is in said first position thereof.

8. A device as claimed in claim 6, further comprising seal means sealing said second ends of said first and second passages and said single opening when said cover is in said first position thereof.

9. A urine suction and collection device for use with a vacuum suction type urinating aid of the type including a urine receiver with a urine suction opening to be applied to the urinating region of a patient, said urine suction and collection device comprising:
a housing having first and second laterally spaced areas;
a suction device for generating a vacuum, said suction device being positioned in said first area of said housing;
a urine tank positioned in said second area of said housing;
a urine transport tube having a first end adapted to be connected to a urine receiver of a vacuum suction type urinating aid and a second end connected to said urine tank;
a vacuum suction tube having a first end connected to said suction device and a second end connected to said urine tank; and
said vacuum suction tube having portions positioned within said housing at locations laterally beyond the positions of said urine tank and said suction device, said portions being of dimensions such that, upon tipping or turning over of said housing, urine within said urine tank will be prevented from reaching said suction device.

10. A device as claimed in claim 9, wherein said vacuum suction tube includes a said portion inclined upwardly from a position adjacent said urine tank to a position adjacent said suction device.

11. A device as claimed in claim 9, further comprising a cover pivotally connected to said housing for selective pivotal movement between a first position covering said second area of said housing and a second position uncovering said second area whereat said urine tank may be inserted into and removed from said second area, means in the bottom of said cover for supporting said second ends of said urine transport tube and said vacuum suction tube, and opening means in the top of said urine tank for communication therethrough of said second ends of said urine transport tube and said vacuum suction tube when said cover is in said first position thereof, whereby pivotal movement of said cover between said first and second positions thereof moves said second ends of said urine transport tube and said vacuum suction tube away from said opening means.

12. A device as claimed in claim 11, wherein said opening means comprise first and second openings in said top of said urine tank, and said supporting means comprise first and second passages extending through said cover and having first ends respectively connected to said second ends of said urine transport tube and said vacuum suction tube and second ends respectively opening downwardly into said first and second openings when said cover is in said first position thereof.

13. A device as claimed in claim 12, wherein said second end of said first passage extends through said first opening in said top of said urine tank and protrudes into said urine tank when said cover is in said first position thereof.

14. A device as claimed in claim 12, further comprising first and second seals respectively sealing said second end of said first passage and said first opening and said second end of said second passage and said second opening when said cover is in said first position thereof.

15. A device as claimed in claim 11, wherein said opening means comprises a single opening in said top of said urine tank, and said supporting means comprise first and second passages extending through said cover and having first ends respectively connected to said second ends of said urine transport tube and said vacuum suction tube and second ends opening downwardly into said single opening when said cover is in said first position thereof, said second end of said first passage being positioned coaxially within said second end of said second passage.

16. A device as claimed in claim 15, wherein said second end of said first passage extends through said single opening and protrudes into the interior of said urine tank when said cover is in said first position thereof.

17. A device as claimed in claim 15, further comprising seal means sealing said second ends of said first and second passages and said single opening when said cover is in said first position thereof.

18. A device as claimed in claim 9, wherein said first and second areas comprise first and second laterally separated compartments in said housing.

* * * * *